Figure 1:
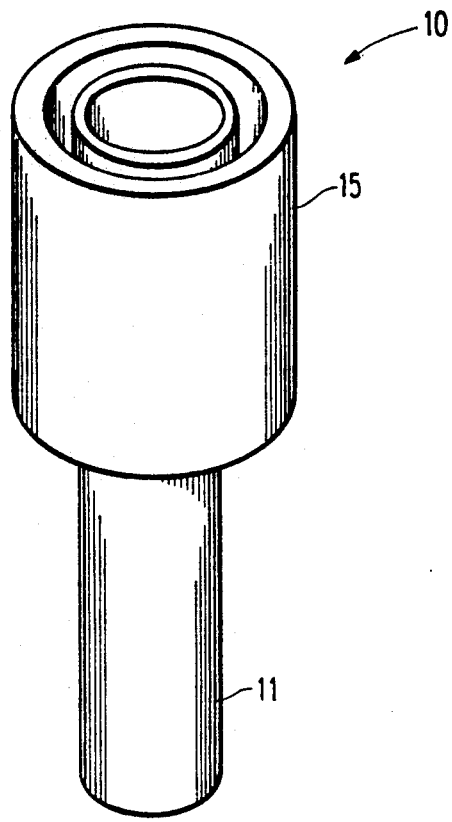

United States Patent [19]

Babson

[11] Patent Number: 5,258,309

[45] Date of Patent: *Nov. 2, 1993

[54] PROCEDURE FOR AUTOMATED SOLID-PHASE IMMUNOASSAY USING A CENTRIFUGE TUBE

[75] Inventor: Arthur L. Babson, Chester; John E. Underwood, Ramsey, both of N.J.

[73] Assignee: Cirrus Diagnostics, Inc., Chester, N.J.

[*] Notice: The portion of the term of this patent subsequent to Mar. 24, 2009 has been disclaimed.

[21] Appl. No.: 779,845

[22] Filed: Oct. 21, 1991

Related U.S. Application Data

[60] Continuation of Ser. No. 552,132, Jul. 13, 1991, Pat. No. 5,098,845, division of Ser. No. 223,337, Jul. 25, 1988, abandoned.

[51] Int. Cl.$^5$ .................. G01N 35/00; G01N 30/96
[52] U.S. Cl. ............................... 436/45; 422/69; 422/71; 422/72; 494/37
[58] Field of Search ............. 422/69, 71, 72; 436/45; 494/37, 43, 44

[56] References Cited

U.S. PATENT DOCUMENTS

| | | | |
|---|---|---|---|
| 3,722,790 | 3/1973 | Natelson | 494/37 X |
| 3,826,622 | 7/1974 | Natelson | 422/72 X |
| 3,841,838 | 10/1974 | Natelson | 422/102 |
| 4,177,921 | 12/1979 | Nielson | 494/44 |
| 4,244,694 | 1/1981 | Favina et al. | 422/72 X |
| 4,314,968 | 2/1982 | Guigan | 436/45 X |
| 4,458,812 | 7/1984 | Dreier et al. | 494/44 |
| 4,470,954 | 9/1984 | Chiknas | 422/72 |
| 4,478,946 | 10/1984 | Van der Merwe et al. | 436/524 |
| 4,639,242 | 1/1987 | Babson | 494/37 |
| 4,753,775 | 6/1988 | Ebersole et al. | 422/69 X |
| 4,758,409 | 7/1988 | Uffenheimer | 422/102 |
| 4,879,242 | 11/1989 | Tsukioka | 436/54 |
| 4,939,096 | 7/1990 | Tonelli | 435/5 |
| 5,098,845 | 3/1992 | Babson | 436/45 |

Primary Examiner—Lyle A. Alexander
Assistant Examiner—A. Soderquist
Attorney, Agent, or Firm—Whitham & Marhoefer

[57] ABSTRACT

A method for conducting immunoassays in an automated fashion is disclosed. A biological fluid under test is placed in a tube (11) which has a solid support (18) therein to which a specific analyte in the biological fluid will be selectively bound. After the analyte in the biological fluid is bound to the solid support (18), the tube (11) is rotated at high speed about its longitudinal axis causing the biological fluid to be transported up the inside walls of tube (11), over the open terminal end (16), and into waste chamber (15). The solid support (18) with the bound analyte may easily be washed by flushing the inside of tube (11) with water or other suitable fluids and rotating the tube (11) at high speed about its longitudinal axis.

5 Claims, 1 Drawing Sheet

PROCEDURE FOR AUTOMATED SOLID-PHASE IMMUNOASSAY USING A CENTRIFUGE TUBE

This application is a continuation of the copending application having Ser. No. 07/552,132, filed Jul. 13, 1991, now U.S. Pat. No. 5,098,845, which was a divisional application of the application having Ser. No. 07/223,337, filed Jul. 25, 1988, now abandoned.

A number of procedures in clinical, diagnostic laboratories, as well as other laboratories in which assays of materials are conducted, require centrifugation—the separation of materials of varying densities in a suspension by the use of centrifugal force. In the clinical laboratory, an example of the use which centrifuges are put is the procedure for the clarification and removal of sediments, cells, and interfering proteins from solutions and colloids by specific precipitation reagents. In such instances, using conventional horizontal centrifuges, a sample container of the mixture is placed in a holder called a "bucket". These buckets are subsequently attached to a vertical rotor and swung to a horizontal plane under centrifugal force. At this point of the centrifugation, the denser particles in the sample move along an unimpeded path toward the bottom of the container to form a smooth, even "pellet" which allows for easy decanting of the non-pelleted supernatant solution once the process is halted.

A second rotor type is the fixed angle rotor which holds the sample container at an angle to the center of rotation. The denser particles in such a rotor will pellet along the side wall of the container making decanting of the supernatant more difficult because of the possible resuspension of the pellet. There are certain advantages in using such a rotor—a shorter path for sedimentation (resulting in a shorter time for separation) and the possibility of obtaining higher speeds and centrifugal force (as a result of less air turbulence).

A disadvantage of both types of centrifugation is the need to balance each bucket accurately in order to prevent damage to the rotor and the centrifuge at the high speeds obtained by the rotors.

In my earlier U.S. Pat. No. 4,639,242, the complete disclosure of which is incorporated herein, I described a vessel which would allow for the complete physical separation of the precipitate and the supernatant solution in a single tube which, acting as a centrifugation tube, was designed to spin about its longitudinal axis forcing the contents of the tube against the inner wall of the tube. As the tube spun, the liquid and precipitate contained within the tube were forced upwards towards the top of the tube where the precipitate would be deposited and retained within the V-grooves on the tube's interior.

The present invention is an improvement over my earlier patented vessel, and provides a unique and novel single-use disposable container for performing solid-phase immunoassays. The vessel, according to the present invention, may also be easily adapted for the purification of various proteins of biological interest by providing a means for the separation of the desired proteins from liquid samples by affinity chromatography.

As a general rule, immunoassays in the clinical laboratory have rapidly replaced other methods used to detect or quantitate substances in body fluids with important biologic or pharmacologic properties. The high levels of sensitivity and specificity achieved with immunoassays result from the specific, high-affinity reversible binding of antigens to antibodies, and from the development of methods for attaching readily detected labels (radioactive isotopes, fluorescent or chemiluminescent molecules, enzymes and the like) to antigens or antibodies. Although radioactive isotopes have been the most extensively used label, they are not preferred because of concerns with radioactivity. Because of these concerns, the number of sensitive, specific immunoassays employing non-radioactive labels is rapidly expanding.

As is generally known among clinicians, many immunoassay procedures are based upon the reaction of an antigen (the analyte to be ultimately measured) with an antibody which has been adsorbed or otherwise bound to a solid surface. These solid surfaces (hence the designation "solid-phase immunoassays") may be the interior of small test tubes (such as those available from Micromedic Systems, Inc. of Horsham, Pa), microtiter trays (such as the 96 well trays available from Amersham International of Bucks, England), macrobeads (such as those available from Abbott Laboratories of Abbott Park, Ill.), or microparticles (such as those available from Pandex Laboratories, Inc of Mundolein, Ill.), or magnetic particles (such as those available from Corning Medical of Medfield, Mass.). An advantage of solid-phase immunoassay over liquid-phase immunoassay is that common reagents and serum constituents which can potentially interfere with the measurement of the label are removed in the washing step of the procedure.

While a variety of immunoassay schemes involving a solid-phase reactant are possible, most schemes utilize a solid-phase antibody and are generally classified as competitive or noncompetitive.

In competitive immunoassays (which are generally used for small molecular weight analytes with only a single antibody binding site) antigen present in the sample or standard competes with a measured amount of labelled antigen for a limited number of binding sites on a solid-phase bound antibody. After removal of any unreacted antigen from the test system, and washing of the solid support material, the bound label is quantitiated by suitable means well known in the art. The amount of labelled antigen bound to the solid-phase antibody is inversely related to the concentration of antigen (analyte) in the sample or standard.

In noncompetetive immunoassays, an excess of labelled antibody binds to essentially all of the analyte present in the sample, and any excess of the solid-phase antibody also binds to additional sites on the analyte. These two separate antigen-antibody reactions can be conducted either sequentially, by providing an intermediate washing step if the first reaction is with solid-phase antibody, or simultaneously. After the immunological reactions are allowed to reach equilibrium, the excess labelled antibody is removed, the solid phase is washed and the bound label quantitated by suitable means well known in the art. This type of immunoassay is also called a "sandwich assay" because the antigen is sandwiched between the solid-phase and labelled antibodies. It is also called "immunometric assay" because the amount of label bound is usually a direct and linear function of the antigen concentration within the sample. It is also called "two-site immunoassay" if the labelled and solid-phase antibodies are directed to distinct antigenic determinants on the analyte. This type of assay can only be used with large molecular weight analytes with multiple antibody binding sites.

In an alternative sandwich assay format, the second antibody is unlabeled and the procedure is expanded to include an incubation of the sample with an excess of labelled third antibody specific for the IgG of the animal species from which the second antibody is elicited. In this instance, the immobilized and second antibodies are obtained from different animal species, in order to prevent the binding of labelled third antibody directly to the immobilized antibody. An advantage of this approach is that a single labelled antibody can serve as a common reagent for a number of analytes.

Common to all solid-phase immunoassays is the requirement that all unbound labelled antigen or antibody must be removed by thorough washing of the solid phase prior to measurement of the label. This required washing is a cumbersome procedure particularly for automated analytical systems. For example, washing coated tubes or microwells by alternately adding and aspirating water or wash solution (as is customarily done) is inefficient as there is always some residual solution in the tube or well after each wash cycle. As many as four to six washes of about 4 ml are required to adequately wash the coated tubes conventionally used in present day immunoassay procedures. Furthermore, provisions must be made to collect all the used wash solutions as they could possibly contain infectious agents from the sample specimens.

In actual use, the vessel according to the present invention offers a number of advantages not found in present protocols and apparatus conventionally used in solid-phase immunoassay procedures which will become readily apparent to those skilled in the art. For example, in the vessel according to the present invention, all excess sample, reagents and wash solution is retained in the individual vessel; when spun at very high speed along the longitudinal axis of the vessel, the removal of excess sample, reagent and wash solution is extremely efficient—no residue of solution remains in the bottom of the tube; sequential, multiple washings can be done as rapidly as the wash solution can be repetitively pipetted into the central tube of the vessel as the transfer to the waste collection chamber of the vessel is almost instantaneous with the addition of solution into the tube; and owing to the speed with which washing is accomplished, multiple vessels may be processed sequentially without impairing sample throughput—a feature allowing for the precise control of the incubation times required by immunoassays, and allowing for the normally labor-intensive immunoassay procedure to be automated.

Figure 2:
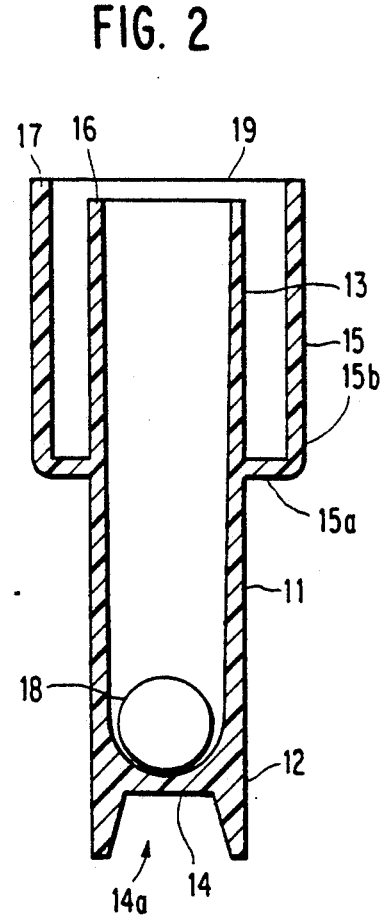

The various aspects, advantages, and principles of the present invention, and the preferred embodiments thereof, will be best understood by reference to the accompanying drawings in which:

FIG. 1 is a perspective view of the vessel incorporating the teachings of the present invention; and FIG. 2 is a longitudinal cross sectional view of the vessel according to the present invention.

Referring to the figures, the vessel according to the present invention is generally shown at 10 as comprising a longitudinally extending central tube 11 opened at its upper end portion 13, and sealed at its lower end portion 12. Integrally attached to tube 11 at a midportion between the upper and lower ends is a generally cylindrical waste chamber or chamber 15 having a circumfrentially extending bottom portion 15a extending between tube 11 and the waste chamber's upwardly extending cylindrical side wall 15b, open at its uppermost end 17; the chamber being coaxial with the tube 11, and having a inner diameter greater than the outer diameter of the tube. Although the vessel may be manufactured from various materials, for ease of manufacture it is preferred that the vessel be molded from a plastic (polymeric) material which is compatible with its intended use. The uppermost end of waste chamber 15 is preferably sealed with a metal foil or polymeric membrane 19 to contain the liquid in the vessel as it is spun on its longitudinal axis. Prior to use, the center of the membrane 19 is punctured to allow addition of the sample and reagents to tube 11.

The lower end 12 of the vessel 10 is adapted to have an engagement means 14 for engaging the vessel with a rotating axle member (not shown) to allow the vessel to be spun on its longitudinal axis. As depicted in the figure (although the depiction is for illustration purposes only and the actual engagement means may take other forms), means 14 comprises a female socket 14a adapted to fit in frictional engagement about a male rotor axle to provide a union with the spinning rotor axle and thereby provide for the spinning of the vessel about its longitudinal axis. As the vessel is spun about its axis, any fluid within the central tube 11 will travel upward along the inner surface of the tube (which is preferably manufactured in such a manner so that the closed bottom of the tube has a slightly smaller inner diameter than the open top of the tube, thereby aiding in the travel of the fluid upward along the inner surface of the tube). As can be seen in the FIG. 2, the uppermost terminal end 16 of tube 11 is short of the cross-sectional plane passing through and defining the open uppermost end 17 of the chamber 15, thus allowing for any fluid being spun out of tube 11 by centrifugal forces when the vessel is spinning about its longitudinal axis to be collected in the waste chamber 15. Waste chamber 15 may also be manufactured in such a manner so that its inner diameter at the bottom portion 15a is slightly greater than its inner diameter at its uppermost end 17, thereby functioning to prevent spillage of fluid out of the chamber as the vessel is being spun about its longitudinal axis. Thus, the centrifugation does not need to be stopped and the tube removed from a "bucket" for decanting of the spent supernatant as must be done with conventional centrifuge techniques—the liquid is being constantly removed from the tube as a result of spinning the vessel about its longitudinal axis. When the vessel according to the present invention is being used in immunoassay procedures, it will be conventional to coat the bottom portion, that is from the very bottom of the closed end of the tube upwards to a point anywhere less than about 25% (the actual length of the coating being a matter of design of the coating process for manufacture of the coated tube) of the overall length of the tube, of the inner surface of the tube with either an antigen or antibody protein. As an alternative to coating the inner surface of the tube with a spcific antigen or antibody, or as a means for providing for additional reaction surfaces for the desired immunoassay procedure, it may be desired to provide a solid support 18 within the tube to which the reactant material within the fluid specimen will bind. Among the additional solid supports which may be utilized are various appropriate antigen or antibody coated spheres of organic polymers or inorganic (such as various silica gels) polymers—the actual functionally equivalent material being a matter of choice dependent upon the binding characteristics of the appropriate antigen or antibody or the ligand used to bind the antigen or antibody to the support.

As depicted in FIG. 2, a metal foil or polymeric membrane seal 19 is preferably placed over the open end of the vessel to contain the liquid in vessel as the vessel is spun on its longitudinal axis; it is envisioned that the vessel may be pre-packaged for use in a specific immunoassay test, and in such an instance the vessel will be sealed at the time of manufacture with the interior surface of the central tube pre-coated with the appropriate antigen or antibody (or alternatively with a coated solid support placed within the central tube). In such a pre-packaged format, the vessel will function as a single-use immunoassay reaction vessel. Prior to use, the center of the membrane is punctured to allow the fluid specimen (which might be urine, blood serum or plasma, or other body fluids or body tissue extracts) along with the proper labelled reagent to be added to tube 11.

As a generalized, but by no means one intending to limit the scope of the present invention, example of how the vessel may be utilized for conducting immunoassays, a sample of fluid containing the analyte to be determined will be added to the vessel's central tube along with a solvent (if required to reconstitute any dry reagent necessary in order to conduct the assay) or the labelled antigen or antibody by either a pipette probe or a hypodermic needle puncturing the seal covering the open end of the vessel. vessel about its longitudinal axis by means of a rotor axle whose speed may be controlled (alternatively, the vessel may be rotated by hand to ensure the sample fluid is thoroughly mixed within the coated tube). After an appropriate incubation period during which time any analyte in the sample will bind to the appropriate antibody on the inner surface of the central tube, the rotor will be rotated at a speed sufficiently great to cause any fluid within the central tube to be transferred into the waste chamber. While the tube is spinning, water or other wash solution may be intermittently introduced into the central tube to wash any remaining sample and reagent out of the tube and into the waste chamber. Once washing is completed, the bound label in the lower portion of the central tube may then be quantitated by suitable means well known in the diagnostic arts.

Of course, the vessel according to the present invention may be used in other procedures besides immunoassays. For example, among the many techniques used today in biochemical separations, perhaps the most efficient and selective is affinity chromatography. Affinity chromatography does not rely on general molecular properties such as size, electrical charge or density to carry out a separation. Instead, it involves a very specific interaction between two biomolecules, one of which is chemically attached (in solid phase separations) to a solid support phase, and the other of which is dissolved in solution. Such interactions are almost a universal feature of biomolecules. Specific examples would include binding between antibodies and antigens, lectins and antigens, hormones and receptors, enzymes and either substrates, coenzymes, inhibitors or activators, DNA and its complement (a repressor or catabolite gene activator for double-stranded DNA or the complement of a single strand of DNA) and messenger RNA and ribosomes. It will be readily apparent to one skilled in the separation art, that the vessel of the present invention may be modified by chemically attaching an appropriate biomolecule to either the inner surface of tube 11 or to the additional solid phase support 18, and utilizing the vessel as an affinity chromatographic separation device—once the interaction between the two biomaterials is completed, the vessel may simply be spun rapidly about its longitudinal axis to remove the unbound biomaterial from the center of the tube into the waste chamber.

Thus, while I have illustrated and described the preferred embodiment of my invention, it is to be understood that this invention is capable of variation and modification, and I therefore do not wish to be limited to the precise terms set forth, but desire to avail myself of such changes and alterations which may be made for adapting the invention to various usages and conditions. Accordingly, such changes and alterations are properly intended to be within the full range of equivalents, and therefore within the purview of the following claims.

Having thus described my invention and the manner and process of making and using it in such full, clear, concise, and exact terms so as to enable any person skilled in the art to which it pertains, or with which it is most nearly connected, to make and use the same;

I claim:

1. An automated method for performing a scientific analysis comprising:
   providing a centrifuge tube which has a conical interior wall tapering outwardly from a central vertical axis as said interior wall extends from a closed bottom end of said centrifuge tube to an open top end of said centrifuge tube, a waste chamber connected to said centrifuge tube positioned to catch and hold fluid sprayed from said open top end of said centrifuge tube, and a biomaterial positioned inside said centrifuge tube;
   adding a biological fluid to said centrifuge tube;
   mixing said biological fluid with said biomaterial such that analyte in said biological fluid becomes bound to said biomaterial;
   removing said biological fluid by rotating said centrifuge tube about its longitudinal axis at high speed such that said biological fluid in said tube travels up said conical interior wall of said centrifuge tube and is sprayed outwardly from said open top end of said centrifuge tube;
   washing said biomaterial with a wash fluid;
   removing said wash fluid from said centrifuge tube by rotating said centrifuge tube about its longitudinal axis at high speed such that said wash fluid in said tube travels up said conical interior wall of said centrifuge tube and is sprayed outwardly from said open top end of said centrifuge tube;
   collecting said biological fluid and said wash fluid in said waste chamber during said removing steps;
   stopping the rotation of said centrifuge tube after said biological fluid and said wash fluid have been removed from said centrifuge tube; and
   quantifying an amount of said analyte in said biological fluid.

2. A method as recited in claim 1 wherein said steps of washing said biomaterial and removing said wash fluid from said centrifuge tube are performed simultaneously.

3. A method as cited in claim 1 wherein said step of quantifying comprises an affinity chromatography isolation.

4. A method as recited in claim 1 wherein said step of quantifying comprises a competitive immunoassay.

5. A method as recited in claim 1 wherein said step of quantifying comprises a non-competitive immunoassay.

* * * * *